US007189556B2

(12) United States Patent
Venkateswaran et al.

(10) Patent No.: US 7,189,556 B2
(45) Date of Patent: Mar. 13, 2007

(54) BACILLUS ODYSSEYI ISOLATE

(75) Inventors: Kasthuri Venkateswaran, Arcadia, CA (US); Myron Thomas La Duc, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/759,327

(22) Filed: Jan. 17, 2004

(65) Prior Publication Data

US 2004/0158042 A1   Aug. 12, 2004

Related U.S. Application Data

(60) Provisional application No. 60/440,790, filed on Jan. 17, 2003.

(51) Int. Cl.
*C12N 1/20* (2006.01)
(52) U.S. Cl. ................................. 435/252.5; 424/93.46
(58) Field of Classification Search ...................... None
See application file for complete search history.

(56) References Cited

OTHER PUBLICATIONS

La Duc, M. et al (Characterization of microbes intimately associated with the Mars Odyssey Orbiter and it's assembly facility, Abstracts of the general meeting of the American Society for Microbiology, 2002; 102: 389).*
Venkateswaran, K. et al (*Bacillus nealsonii* sp. nov., isolated from a spacecraft-assembly facility, whose spores are g-radiation resistant, International Journal of Systematic and Evolutionary Microbiology, Jul. 2002; 53: 165-172).*
Allen et al, Section VI, Isolation and Examination of Anaerobic Bacteria, Manual of Clinical Microbiology, Fourth Edition, 1985, p. 413-14.*
Anonymous, (1980) NASA Standard Procedures for the Microbiological Examination of Space Hardware, NHB 5340.1B, 1980, Jet Propulsion Latoratory communication, National Aeronautics and Space Administration, pp. 2-26.
La Duc M.T., Nicholson W., Kern R., and K. Venkateswaran (2003) Microbial Characterization of the Mars Odyssey Spacecraft and Its Encapsulation Facility. Environ Microbiol, Oct. 5, 2003 p. 977 Abstract only; entire article not provided.
Nicholson, W. L., Munakata, N., Horneck, G., Melosh, H. J. and Setlow, P. (2000) Resistance of *Bacillus* endospores to extreme terrestrial and extraterrestrial environments. Microbiol Mol Biol Rev 64: 548-572.
Priest, F. G., Goodfellow, M. and Todd, C. (1988) A numerical classification of the genus *Bacillus*, J Gen Microbiol 234: 1847-1882.

Reisenman, P.J. and Nicholson, W.L. (2000) Role of the spore coat layers in *Bacillus subtilis* spore resistance to hydrogen peroxide, artificial UV-C, UV-B, and solar UV radiation. Appl Environ Microbiol 66: 620-626.
Ruger, H. J., Fritze, D., and Sproer, C. (2000) New psychrophilic and psychrotolerant *Bacillus marinus* strains from tropical and polar deep-sea sediments and emended description of the species. Int J Syst Evol Microbiol 50: 1305-1313.
Schaeffer, P., Millet, J. & Aubert, J.-P. (1965) Catabolic repression of bacterial sporulation. Proc Natl Acad Sci 54:, 704-711.
Swofford, D. (1990) PAUP: phylogenetic analysis using parsimony, version 3.0. Computer program distributed by the Illinois Natural History Survey, Champaign, IL.
Venkateswaran, K., Kempf, M., Chen, F., Satomi, M., Nicholson, W., & Kem. R. (2003) *Bacillus nealsonii* sp. nov., isolated from a spacecraft assembly facility, whose spores are gamma-radiation resistant. Int J Syst Evol Microbiol 53: 165-172.
Venkateswaran, K., Satomi, M., Chung, S., Kern, R., Koukol, R., Basic, C. & White, D. (2001) Molecular microbial diversity of a spacecraft assembly facility. Syst Appl Microbiol 24: 311-320.
Yoon, J.-H., Lee, K.-C., Weiss, N., Kho, Y. H., Kang, K. H. & Park, Y.-H. (2001) *Sporosarcina aquimarina* sp. nov., a bacterium isolated from seawater in Korea, and transfer of *Bacillus globisporus* (Larkin and Stokes 1967), *Bacillus psychrophilus* (Nakamura 1984) and *Bacillus pasteurii* (Chester 1898) to the genus *Sporosarcina* as *Sporosarcina globispora* comb. nov., *Sporosarcina psychrophila* comb. nov. and *Sporosarcina pasteurii* comb. nov., and emended description of the genus *Sporosarcina* . Int J Syst Evol Microbiol 51: 1079-1086.
Ash, C, Wallbanks, S. and Collins, M. D. (1991) Phylogenetic heterogeneity of the genus *Bacillus* as revealed by comparative analysis of small-subunit-ribosomal RNA sequence, Lett Appl Microbiol 13: 202-206.
Ezaki, T., Hashimoto, Y. and Yabuuchi, E. (1989) Fluorometric deoxyribonucleic acid-deoxyribonucleic acid hybridization in microdilution wells as an alternative to membrane filter hybridization in which radioisotopes are used to determine genetic relatedness among bacterial strains. Int J Syst Bacteriol 39: 224-229.

* cited by examiner

*Primary Examiner*—Irene Marx
(74) *Attorney, Agent, or Firm*—Tope-McKay & Associates

(57) ABSTRACT

The present invention relates to discovery and isolation of a biologically pure culture of a *Bacillus odysseyi* isolate with high adherence and sterilization resistant properties. *B. odysseyi* is a round spore forming *Bacillus* species that produces an exosporium. This novel species has been characterized on the basis of phenotypic traits, 16S rDNA sequence analysis and DNA-DNA hybridization. According to the results of these analyses, this strain belongs to the genus *Bacillus* and the type strain is $34\text{hs-}1^T$ (=ATCC PTA-4993$^T$=NRRL B-30641$^T$=NBRC 100172$^T$). The GenBank accession number for the 16S rDNA sequence of strain $34\text{hs-}1^T$ is AF526913.

1 Claim, 5 Drawing Sheets

| Characteristic | 1 | 2 | 3 | 4 | 5 | 6 |
|---|---|---|---|---|---|---|
| Substrate oxidized: | | | | | | |
| Acetate | + | + | + | ND | ND | − |
| Pyruvate | + | + | + | + | − | + |
| α-Hydroxybutyrate | + | − | − | ND | ND | − |
| β-Hydroxybutyrate | + | − | − | + | − | + |
| Methyl pyruvate | + | + | + | ND | ND | − |
| L-Alanine | + | + | + | − | − | + |
| Glycyl L-glutamate | + | + | + | − | + | + |
| Adenosine | − | + | + | ND | + | + |
| 2′-Deoxyadenosine | + | + | + | − | + | + |
| Inosine | + | + | + | − | + | + |
| AMP | + | + | + | − | + | − |
| UMP | + | + | + | − | + | − |
| Growth in 5% NaCl | + | + | + | − | + | ND |
| 16S rDNA sequence similarity (%)* | NA | 96.4 | 95.7 | 93.1 | 92.4 | 91.5 |

| Strain | Similarity (%) t labelled DNA from: | | | |
| --- | --- | --- | --- | --- |
| | 1 | 2 | 3 | 7 |
| 1. B. odysseyi 34hs-1[T] | 100 | 18 | 17 | 17 |
| 2. B. fusiformis ATCC 7055[T] | 23 | 100 | 17 | 15 |
| 3. B. silvestris NRRL B-23336[T] | 17 | 18 | 100 | 15 |
| 4. B. pycnus NRRL NRS-1691[T] | 11 | ND | ND | 11 |
| 5. 'B. aminovorans' NRRL NRS-341 | 10 | ND | ND | 16 |
| 6. B. neidei NRRL BD-101 | 7 | ND | ND | 15 |
| 7. B. sphaericus NRRL BD-113 | 7 | ND | ND | 100 |
| 8. Sporosarcina aquimarina SAFN-008 | 7 | ND | ND | 8 |

FIGURE 9

BACILLUS ODYSSEYI ISOLATE

PRIORITY CLAIM

This application is a non-provisional application, claiming the benefit of priority to provisional application No. 60/440,790, filed in the United States on Jan. 17, 2003, entitled "Bacterial spore-forming species that is extremely resistant to various sterilization methods."

GOVERNMENT RIGHTS

This invention was made with Government support under Contract NAS7-1407 awarded by NASA. The Government has certain rights in the invention.

FIELD OF INVENTION

The present invention relates to an isolated biologically pure culture of a novel spore forming *Bacillus* species, and more particularly, to a *Bacillus odysseyi* isolate with high adherence and sterilization resistant properties.

BACKGROUND OF INVENTION

Several physiologically and phylogenetically distinct microorganisms have been encountered while examining microbial contamination of spacecraft surfaces. Some of these micro-organisms form round, exosporium-bearing spores, whose exosporia might be responsible for adaptation to the extreme clean conditions of, and direct adhesion to, spacecraft surfaces.

Such biofouling is a concern in not only space travel, but in a number of industries. Isolation, identification and understanding of the highly resistant and adhesive micro-organisms could be of significant use in industry, where biofouling is a major cause of reduction in productivity (resulting in a loss of over $6.5 billion in marine industries alone), and in medicine, where bacterial adhesion is often a primary step in human disease. In addition, purified exosporium components (proteins, lipids, etc.) could possibly be used in other ways, such as in sunscreens or to prolong the lives of convertible tops, tents, etc. as an Ultra Violet-ray retardant spray.

Additionally, isolation of the microorganism would allow for formation of strategies for inactivating those resistance characteristics that interfere with sterilization of spacecraft materials; in particular, resistance to Hydrogen Peroxide ($H_2O_2$), Ultra Violet (UV), and g-radiation and adhesion. An understanding of these mechanisms will guide the development of sterilization procedures that are targeted to the specific molecules responsible for resistance, and could eliminate the need for unduly harsh methods that jeopardize equipment. A need exists in the art for an improved sterilization procedure that would enable spacecraft to meet planetary protection requirements without a terminal heat sterilization step. This would support implementation of planetary protection policies for life detection missions.

SUMMARY OF INVENTION

The present invention relates to an isolated biologically pure culture of a novel spore forming *Bacillus* species, and more particularly, to a *Bacillus odysseyi* isolate with high adherence and sterilization resistant properties.

Additionally, because of its UV resistant properties, purified exosporium components (proteins, lipids, etc.) of *B. odysseyi* could be used in sunscreens or to prolong the lives of convertible tops, tents, etc. as a UV-ray retardant spray.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to an isolated biologically pure culture of a novel spore forming *Bacillus* species, and more particularly, to *Bacillus odysseyi*.

The following description, taken in conjunction with the referenced drawings and/or tables, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore, it should be noted that unless explicitly stated otherwise, the figures included herein are illustrated qualitatively and without any specific scale, and are intended to generally present the concept of the present invention.

In order to provide a working frame of reference, first a glossary of terms used in the description and claims is given as a central resource for the reader. Next, a discussion of various aspects of the present invention is provided to give an understanding of the specific details.

(1) Glossary

Before describing the specific details of the present invention, a centralized location is provided in which various terms used herein and in the claims are defined. The glossary provided is intended to provide the reader with a general understanding for the intended meaning of the terms, but is not intended to convey the entire scope of each term. Rather, the glossary is intended to supplement the rest of the specification in more clearly explaining the terms used.

The strain disclosed in this description has been deposited in the Agricultural Research Service Patent Culture Collection (NRRL), Northern Regional Research Center, 1815 North University Street, Peoria, Ill. 61604, U.S.A., as NRRL B-30641. The deposit was received by NRRL on Feb. 4, 2003, and was given an accession number by the International Depository Authority of NRRL B-30641. The deposit has been made to and received by the International Depository Authority under the provisions of the Budapest Treaty, and all restrictions upon public access to the deposit will be irrevocably removed upon the grant of a patent on this application.

API 20NE Test Strips—The term "API 20NE" refers test strips that are used for 24–48 hour identification of gram-negative Enterobacteriaceae.

DNA-DNA hybridization—The term "DNA-DNA hybridization" refers to a technique that provides for genetic comparisons integrated over the entire genome of two species.

Gram-positive—The term "gram positive" refers to bacteria that are stained dark blue or violet by gram staining, in contrast to gram negative bacteria which are not stained dark blue or violet by gram staining. The stain is caused by a higher amount of peptidoglycan in the cell wall, which typically lacks the secondary membrane and lipopolysaccharide layer found in other bacteria.

(2) Introduction

This specification describes *Bacillus odysseyi* sp. nov., isolated from the surface of the Mars Odyssey spacecraft, whose round spores are resistant to Ultra Violet (UV) and gamma radiation, Hydrogen Peroxide ($H_2O_2$) and desiccation. The *Bacillus* strain isolated and described herein was characterized based on a polyphasic taxonomic approach that examined its phenotypic and genotypic affiliations. It is readily apparent to those skilled in the art that within nature, various modifications and variations occur to any given organism and that the description described herein may be altered to account for any modifications or variations.

The strain disclosed in this description has been deposited in the Agricultural Research Service Patent Culture Collection (NRRL), Northern Regional Research Center, 1815 North University Street, Peoria, Ill. 61604, U.S.A, as NRRL B-30641$^T$.

The subject culture has been deposited under conditions that assure that access to the cultures will be available during the pendency of this patent application to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested due to the condition of the deposit(s). All restrictions on the availability to the public of the subject culture deposits will be irrevocably removed upon the granting of a patent disclosing them.

A. Method

The methods for collection, isolation and characterization described herein are for illustrative purposes only. It must be understood that the species *B. odysseyi* may be collected and isolated from any surface where the bacteria is present and that there may be other techniques for characterizing the species. The following techniques are non-limiting examples for completing the described process or technique.

(i) Sample Preparation and Isolation of Microbes from the Mars Odyssey Spacecraft.

Components of the Mars Odyssey spacecraft were manufactured in various geographic locations. The spacecraft underwent several months of assembly in the Spacecraft Assembly Facility at the Jet Propulsion Laboratory, Pasadena, Calif., USA, before it was transported to the Kennedy Space Center, Fla., USA. Samples were taken from 25 different surface areas (25 $cm^2$) of the spacecraft using sterile, water-moistened polyester swabs during final assembly and encapsulation in the Spacecraft Assembly and Encapsulation Facility II, Kennedy Space Center (February 2001). Upon collection of a surface sample, each swab was placed individually into sterile water, creating a final volume of 10 ml (i.e. swab plus sterile water). The 25 samples were pooled into one sterile container and processed immediately. All samples were analyzed for both spore-formers and total cultivable heterotrophs.

(ii) Microbial Examination.

As a non-limiting example of microbial examination, samples were sonicated for 2 minutes (min.) and heat-shocked at 80° C. for 15 min., at which time appropriate aliquots were placed into Petri dishes and total aerobic spores were enumerated by pour-plate techniques using Tryptic Soy Agar (TSA) as the growth medium (32° C. for 2 days). Samples that were not heat-shocked were enumerated for total aerobic cultivable heterotrophs on TSA. Colony forming units (c.f.u.) were counted after incubation at 32° C. for up to 7 days. Isolates were selected, purified, and stored in glycerol at −80° C. Identification of purified strains was accomplished by ribosomal DeoxyriboNucleic Acid (rDNA) sequencing (see below). Type strains of various *Bacillus* species for use as controls were either procured from the American Type Culture Collection or received as gifts from the USDA Research Centre (National Center for Agricultural Utilization Research) collection.

(iii) Sporulation.

As a non-limiting example of sporulation, a Nutrient Sporulation Medium (NSM) was used to produce spores. A single purified colony of the strain to be sporulated was inoculated into NSM liquid medium. After 2–3 days growth at 32° C., cultures were examined in wet mounts to ascertain the level of sporulation. Once the number of free spores was greater than the number of vegetative cells, the culture was harvested and spores were purified. Spores were purified by treating with lysozyme and washing with salts and detergents. These chemical treatments did not remove the exosporium surrounding the spore coat. Purified spores were re-suspended in sterile de-ionized water, heat-shocked (80° C. for 15 min.) to ensure inactivation of the vegetative population and stored at 4° C. in glass tubes.

(iv) Microscopy.

As a non-limiting example of microscopy, the refractile nature of the spores was examined by phase-contrast microscopy. Non-destructive examination of spores and vegetative cells was also exploited using a field-emission environmental Scanning Electron Microscope (SEM). In addition, a standard SEM and a Transmission Electron Microscope (TEM) were utilized to examine surface details and cross sections, respectively, according to established methods.

(v) Characterization of Spores for Various Physical and Chemical Conditions.

As a non-limiting example of spore characterization, radiation dosimetry at the $Co^{60}$ source was performed using an ion chamber with accuracy to the USA Bureau of Standards. All irradiations were carried out in glass vials using spore samples in water. Spores ($10^8$ spores $ml^{-1}$) were exposed to both 1 Mega rad (Mrad) (50 rad $s^{-1}$ for 330 min.) and 0.5 Mrad (25 rad $s^{-1}$ for 330 min.) and survival was quantitatively verified by growing the gamma radiation-treated samples on TSA at 32° C.

Purified spores ($10^6$ spores $ml^{-1}$) were diluted in Phosphate Buffered Saline (PBS) (pH 7.2), placed in an uncovered Petri dish and exposed to UV radiation (254 nm). At appropriate intervals, samples of spores were removed, diluted serially tenfold in PBS and plated onto NSM agar medium. Plates were incubated at 37° C. for up to 5 days and colonies were counted. A liquid $H_2O_2$ protocol, developed by Riesenman & Nicholson (2000), was modified and used to examine $H_2O_2$ resistance in spores. Known concentrations of spore suspensions prepared in PBS ($10^8$ spores $ml^{-1}$) were treated with $H_2O_2$ (5% final concentration) and incubated at room temperature (~25° C.) with gentle mixing. After 60 min incubation, 100 μl was removed and diluted in bovine catalase (100 μg $ml^{-1}$ in PBS). Serial 1:10 dilutions of the catalase treated suspension were prepared in Tryptic Soy Broth (TSB) to check viability and spread onto TSA for quantitative measurement of $H_2O_2$-resistant spores.

To test desiccation resistance, spore suspensions (20 μl) were dispensed onto pre-sterilized metal and glass-fibre discs ($10^3$ spores per disc). The spore inoculated discs were incubated in a glass desiccation chamber with a relative humidity of 15% for 1 or 2 days before c.f.u. were counted on TSA medium. Briefly, the desiccated sample was placed in sterile PBS, vortexed thoroughly and placed in a sonicating water bath for 2 min at room temperature before plating onto TSA medium. Plates were incubated at 32° C. for 2 days and the number of spores that survived was counted. Untreated aliquots of purified spores at equivalent concentrations were included and worked up alongside test aliquots for all treatments as a means of determining relative percentage survivability.

B. Systematic Characterization (i) Phenotypic Characterization.

The ability to grow in NaCl concentrations of 1–10% was determined in $T_1N_1$ liquid medium (1% Bacto tryptone containing the appropriate amount of NaCl) and the ability to grow without NaCl was determined in 1% sterile tryptone water. The commercially available Biolog identification system was used, according to the manufacturer's specifications, to characterize utilization of various carbon substrates. In addition, API 20NE test strips were used to characterize the strain further.

(ii) 16S rDNA Sequencing.

Approximately 10 nanograms (ng) of purified DeoxyriboNucleic Acid (DNA) from liquid cultures was used as a template for Polymerase Chain Reaction (PCR) amplification. Universal primers (Bact 11 and 1492) were used to amplify the 1.5 kilobase pair (kb) PCR fragment. Purified amplicons were sequenced and the identity of a given PCR product was verified by bi-directional sequencing analysis. The phylogenetic relationships of organisms covered in this description were determined by comparison of individual 16S rDNA sequences to existing sequences in public databases, such as the database of the National Center for Biotechnology Information. Evolutionary trees based on parsimony and maximum-likelihood analyses were constructed with Phylogenetic Analysis Using Parsimony (PAUP) software.

(iii) DNA-DNA Hybridization.

Cells were suspended in 0.1 Mole (M) of Ethylenediamine Tetraacetic Acid (EDTA) (pH 8.0) and cell walls were digested by lysozyme treatment (final concentration, 2 mg $ml^{-1}$). DNA was isolated by standard procedures. DNA-DNA relatedness was studied by microplate hybridization methods with photobiotin labeling and colorimetric detection, using 1,2-phenylenediamine as the substrate and streptavidin-peroxidase conjugate as the colorimetric enzyme.

C. Results and Discussion (i) Microbial Examination of the Mars Odyssey Spacecraft.

The microbial population of the large surface area of the spacecraft showed, on average (25 determinations), total heterotrophs and spore-formers at 28.0±8.6 and 2.0±1.5 c.f.u. per 25 $cm^2$, respectively. Isolates were identified by 16S rDNA sequence analysis as species of *Acinetobacter, Bacillus, Curtobacterium, Delftia, Microbacterium* and *Ralstonia*. Additionally, all fungal isolates were identified as *Aureobasidium pullulans* by 18S rDNA sequence analysis. When purified strains arising from isolated colonies were screened for resistance to harsh conditions, such as UV, gamma radiation, $H_2O_2$ and desiccation, several spore-forming isolates showed resistance. Of the 45 strains identified, one strain, designated 34hs-1, exhibited distinct spore morphology and was characterized further for its phylogenetic affiliation.

(ii) Morphological and Physiological Characteristics.

Figure 1:
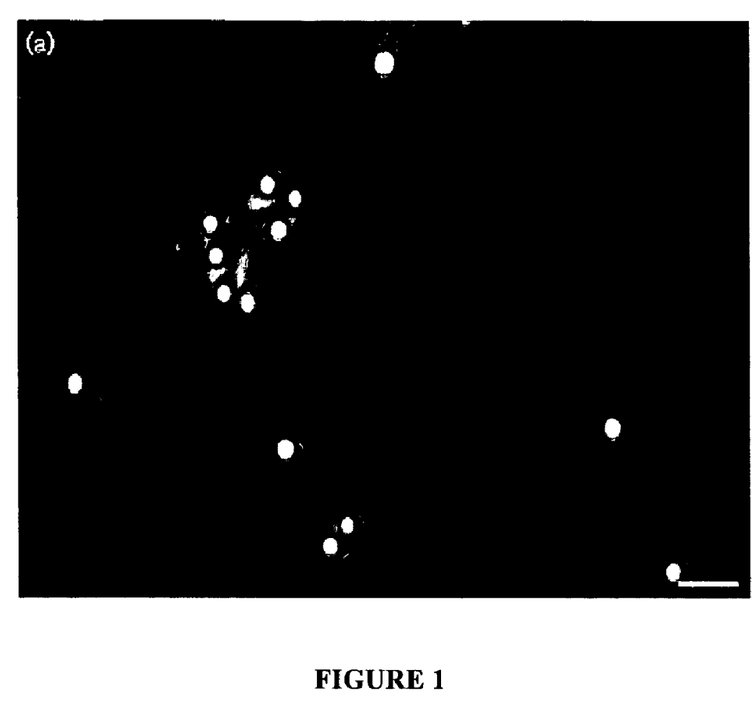
FIG. 1 is a light microscopy image of sporulating vegetative cells showing terminal swelling of mother cells.

Strain 34hs-1 is a Gram-positive, aerobic, rod-shaped, spore-forming bacterium. Cells are 4–5 mm long, 1 mm in diameter and motile. On TSA medium incubated at 32° C., young colonies are beige, round, ~3 mm in diameter, fairly smooth and flat with entire edges. As shown in FIG. 1, endospores of strain 34hs-1 (1 mm in diameter) are terminal, with one spore per cell, and swell the mother cell.

Figure 2:
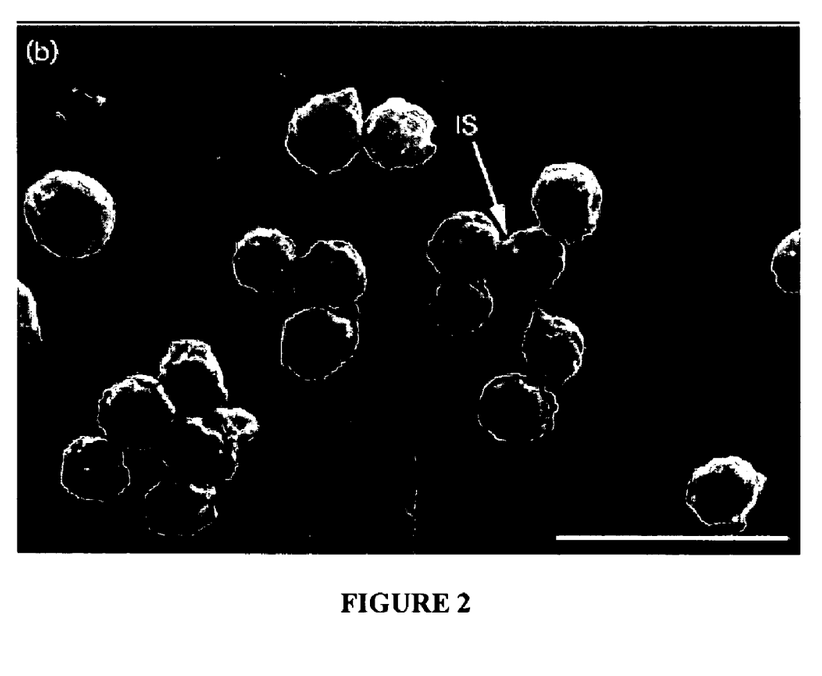
FIG. 2 is a microscopy image of a purified spores showing an intact spore with exosporium.

Additionally, as shown in FIG. 2, the endospores are round. An intact spore is shown, labeled as IS.

Figure 3:
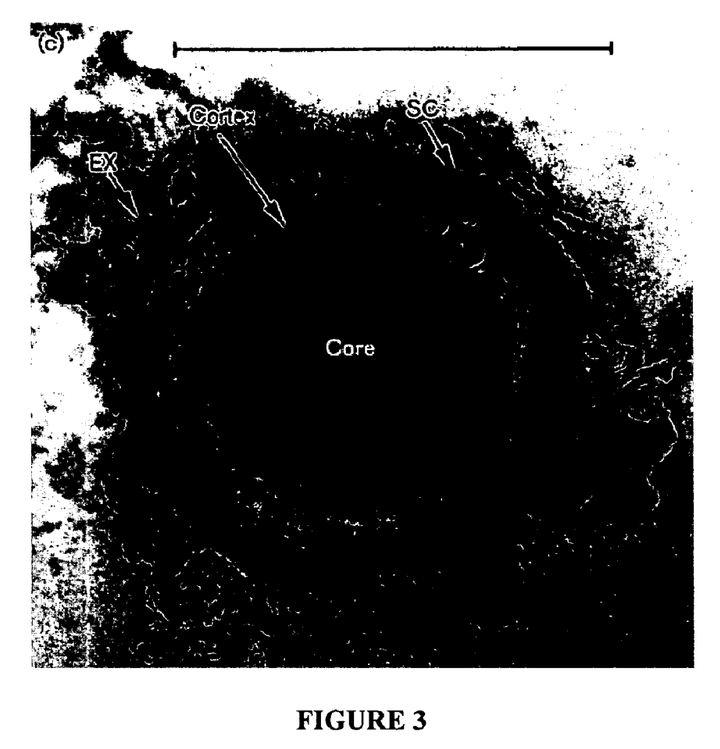
FIG. 3 is a microscopy image of a longitudinal section of an untreated spore, showing the exosporium, spore coat, cortex and spore core.

As shown in FIG. 3, ultrathin sections of spores of strain 34hs-1 showed the presence of an exosporium (labeled in FIG. 3 as EX), a spore coat (labeled in FIG. 3 as SC), a cortex (labeled in FIG. 3 as Cortex) and a core (labeled in FIG. 3 as Core).

Figure 4:
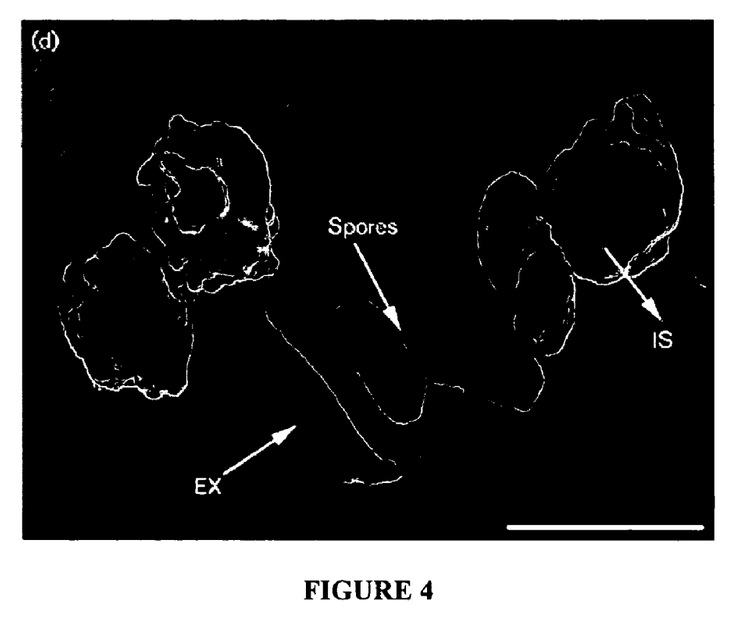
FIG. 4 is a microscopy image of spores after being exposed to gamma radiation.
Figure 5:
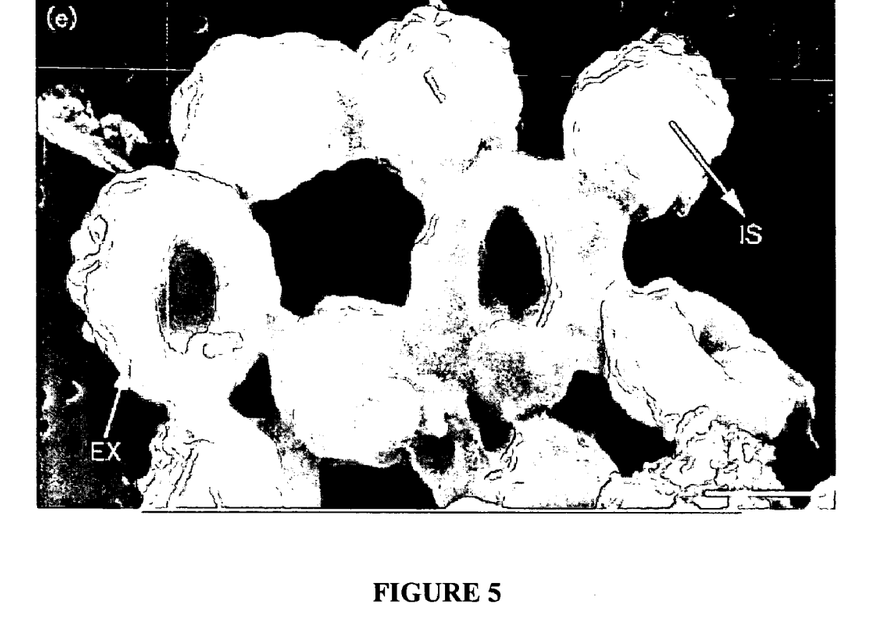
FIG. 5 is a microscopy image of spores after being exposed to $H_2O_2$.
Figure 6:
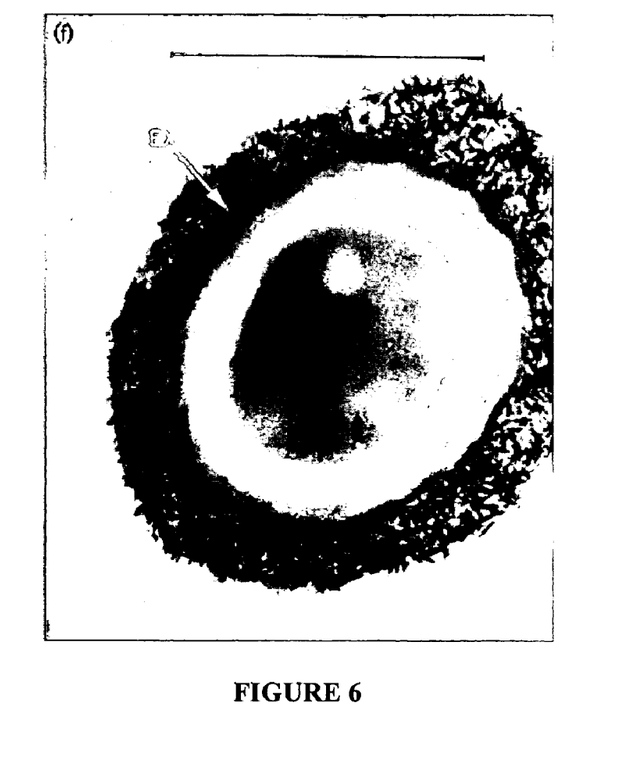
FIG. 6 is a microscopy image of spores after being exposed to both gamma radiation and $H_2O_2$.

As shown in FIG. 4, microscopic analyses revealed the partial destruction of 34hs-1 spores by gamma radiation, although remnants of exosporia were left behind; some spores oxidized by $H_2O_2$ formed 'doughnut-like' structures (Shown in FIG. 5). Further analysis showed highly electron-dense structures in the exosporia (EX) of gamma-irradiated and $H_2O_2$-treated (Shown in FIG. 6) spores when compared with the untreated control shown in FIG. 3.

(iii) Resistance of Spores of Strain 34hs-1 to Various Physical and Chemical Conditions.

The resistance of *Bacillus* spores to a variety of conditions is well documented. Spores of 34hs-1 exhibited resistance to $UV_{254}$ (254 nm UV radiation), gamma radiation, 5% liquid $H_2O_2$ and desiccation conditions. Spores of 34hs-1 did not exhibit classic $UV_{254}$ inactivation kinetics: the characteristic 'shoulder' was missing and inactivation did not take effect until well after 400 J $m^{-2}$. Spores of strain 34hs-1 exhibited an $LD_{90}$ (90% lethal dose) of ~660 J $m^{-2}$. Spores of 34hs-1 also survived 0.5 Mrad gamma radiation (0.4% survival). Purified spores exposed to 5% liquid $H_2O_2$ showed resistance, with nearly 26% of the initial inoculum ($1.1 \times 10^7$ ml$^{-1}$) viable after 60 min exposure. Finally, desiccation had no effect on viability of the 34hs-1 spores. When compared with *Bacillus subtilis* strain 168, spores of strain 34hs-1 appeared to be quite resistant, respectively exhibiting 3, 10, 6, and 10 times greater survival when exposed to UV, gamma radiation, $H_2O_2$, and desiccation, respectively. It is apparent that micro-organisms, now shown to withstand appreciable doses of several sterilants, are present on the surface of a spacecraft being sent to Mars, a pristine extraterrestrial system. Perhaps even more intriguing than their ability to withstand decontamination strategies imposed by mankind is the possibility of such resistances allowing them to survive the highly oxidative UV and gamma radiation-rich environments that they will encounter en route to and on the surface of Mars. This presents a large problem to those concerned with planetary protection, i.e. ensuring appropriate levels of spacecraft cleanliness in order to avoid (i) compromising the integrity of in situ and/or sample-return missions and (ii) contamination of pristine extraterrestrial environments with Earth-derived biomatter.

(iv) Phenotypic Characterization.

Figure 7:
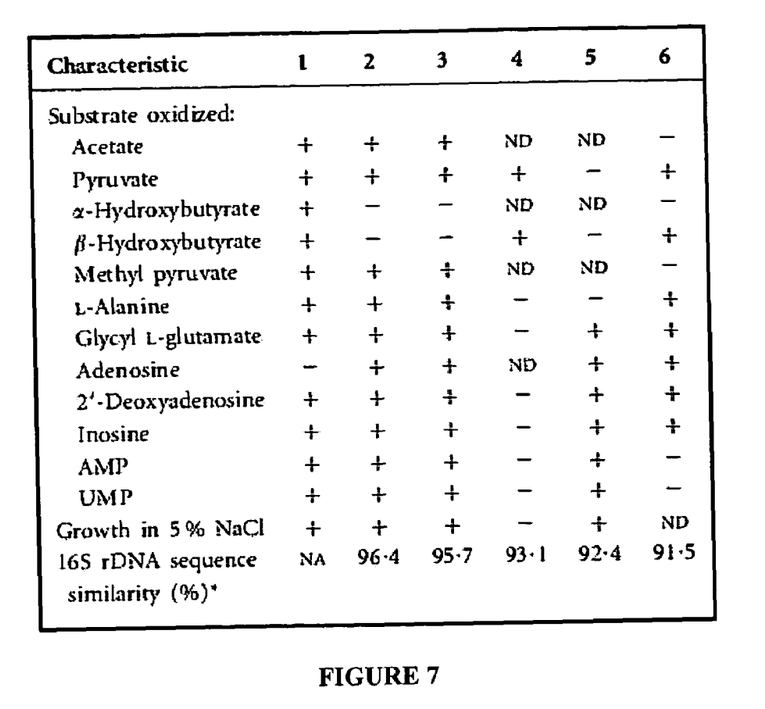
FIG. 7 is a table illustrating characteristics for differentiating *B. odysseyi* 34-hs1 from related species.

Strain 34hs-1 grew between 25 and 42° C., with optimum growth at 30–35° C., and over the pH range 6–10 (optimum 6–7). It did not require Na$^+$ for growth. Biochemical characterization of strain 34hs-1 is presented in FIG. 7; where Strain 1 is *B. odysseyi* 34hs-1; Strain 2 is *B. fusiformis* NRRL NRS-350T; Strain 3 is *B. sphaericus* DSM 28T; Strain 4 is *B. pycnus* NRRL NRS-1691T; Strain 5 is *B. neidei* NRRL BD-87T; and Strain 6 is *B. badius* ATCC 14574T. The row in the table labeled "16S rDNA sequence similarity (%)," refers to the percent similarity of the 16S rDNA sequences of each of the shown strains with that of *B. odysseyi* 34hs-1.

This strain produced catalase, but not cytochrome oxidase, gelatinase, urease, tryptophan deaminase, lysine, ornithine decarboxylase, or arginine dihydrolase. It did not show denitrification or acetoin production. 34hs-1 did not ferment glucose or utilize glucose as a sole carbon source. After prolonged incubation (>3 days), arabinose was assimilated; however, this is not a discriminatory phenotypic trait. Hydrogen sulfide was not produced from thiosulfite. The carbon substrate utilization profile of 34hs-1, as measured by the Biolog system, showed an identification match for *Bacillus badius*. Furthermore, most of the Biolog-generated phenotypic characteristics were similar to those of both *B. sphaericus* and *B. fusiformis* shown in FIG. 7. Strain 34hs-1 did not metabolize common hexoses, pentoses or disaccharides, but preferred pyruvate, amino acids, purine or pyrimidine bases and related compounds as carbon and energy sources. Most round spored *Bacillus* species, including strain 34hs-1, are not able to grow in the absence of oxygen.

(v) Phylogenetic Characterization

The 16S rDNA sequences of all known Firmicutes were compared with that of 34hs-1. All phylogenetic analyses, based on 16S rDNA sequences, unambiguously demonstrated that 34hs-1 belonged to the low-G+C-containing Gram-positive bacteria. The 16S rDNA sequences of all known members of the Gram-positive bacteria were compared with that of 34hs-1. Bootstrapping (500 replicates) analysis was performed to avoid sampling artifacts. The resulting analyses indicated that 34hs-1 shares a close phylogenetic relationship with *Bacillus* species belonging to rRNA group 2. Neighbor-joining, parsimony and maximum-likelihood analyses were undertaken on this subset of bacteria, using several subdomains of the 16S rDNA. In all analyses, strain 34hs-1 was most closely related to members of the genus *Bacillus*.

Similarities in 16S rDNA sequence between 34hs-1 and closely related *Bacillus* species, recognized by GenBank BLAST searches, were 95–96%. GenBank is a nucleotide sequence database maintained by the National Center for Biotechnology Information, located at 8600 Rockville Pike, Bethesda, Md. 20894. Sequence variation of ~3.5% was found between 34hs-1 and *B. fusiformis* ATCC 7055$^T$ and *B. sphaericus* DSM 28$^T$. A very high sequence variation (8%) was observed between 34hs-1$^T$ and *B. subtilis* ATCC 6633. Such a high degree of dissimilarity within a well-described genus is not uncommon. Likewise, *B. badius*, the strain most phenotypically similar to 34hs-1, was only 91.5% similar in 16S rDNA sequence.

Figure 8:
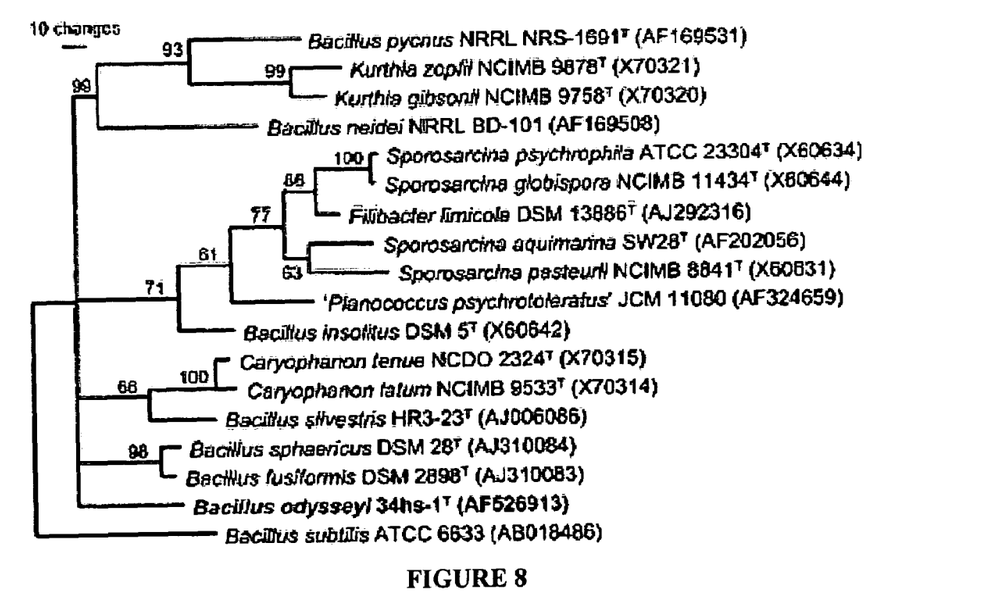
FIG. 8 is a chart illustrating a phylogenetic tree of round-spore forming *Bacillus* and other species closely related to strain 34-hs1 based on maximum likelihood and parsimony analysis of 16S rDNA nucleotide sequences.

A maximum-likelihood phylogenetic tree based on 16S rDNA sequences of several round-spore-forming bacilli, as well as some asporogenous genera, is shown in FIG. 8. Strain number and GenBank accession numbers are shown following the species name respectively. Numbers above the lines are percentage bootstrap values of 500 replications of that branch of the tree. Bar, 10 changes among 1.5 kb, meaning that 10 base pairs changed from one organism to another and required 1,500 million years of evolution.

The branching order of the phylogenetic tree shown in FIG. 8, showed three distinct clusters, in which one clade contained *Kurthia* species, another group was formed from species of *Sporosarcina, Filibacter* and *Planococcus* and a final grouping was composed of species of *Bacillus* and *Caryophanon*, including strain 34hs-1. The round-spore-forming *Bacillus* group was very tightly bound phylogenetically; all members of this clade shared sequence similarities of >95%. Strain 34hs-1 exhibited the characteristics necessary to place it in *Bacillus* rRNA group 2. To differentiate these closely related species more accurately, DNA-DNA hybridization was performed.

(vi) DNA-DNA Hybridization.

Figure 9:
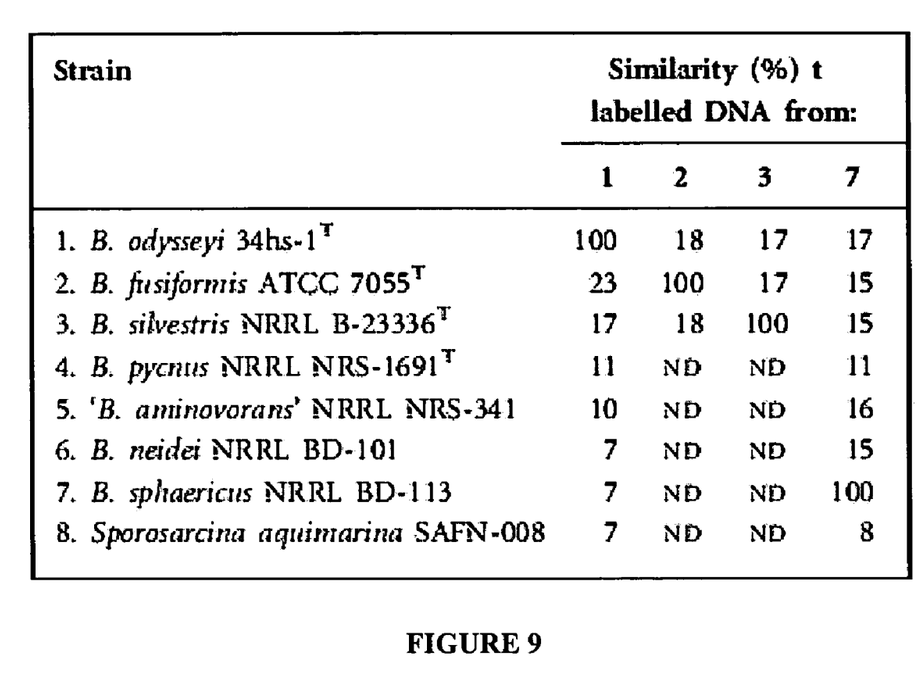
FIG. 9 is a table illustrating DNA-DNA hybridization between *B. odysseyi* sp. Nov. 34-hs1 and related species.

As shown in FIG. 9, DNA-DNA hybridization was performed between 34hs-1 and round-spore-forming *Bacillus* and *Sporosarcina* species. The values shown in FIG. 9 are means of at least two determinations between the two selected species. None of the *Bacillus* species that showed very high 16S rDNA sequence similarities (~96%) exhibited >70% DNA-DNA re-association values with 34hs-1, i.e. the cutoff value required to place strains within the same species. In particular, the hybridization value between 34hs-1 and *B. silvestris* NRRL B-23336T was only 17%, whereas their 16S rDNA sequences were 96.4% similar. Also, strain 34hs-1 and *B. sphaericus* NRRL BD-113 showed 17% DNA-DNA hybridization, but ~97% 16S rDNA sequence similarity. Based on DNA-DNA re-association values, strain 34hs-1 represents a novel *Bacillus* species, *Bacillus odysseyi* sp. nov.

(3) Conclusion

*Bacillus odysseyi* (o.dys.seóyi. L. n. Odyssea the Odyssey; N.L. gen. n. *odysseyi* pertaining to the Mars Odyssey spacecraft, from which the organism was isolated).

Cells are rod-shaped, 4–5 mm in length, approximately 1 mm in diameter and motile. Furthermore, the *B. odysseyi* cells are Gram-positive and aerobic, form terminal endospores, and the spores show an additional exosporium layer. Colonies on TSA are round, smooth, flat with entire edges and beige in color. Sodium ions are not essential for growth; growth occurs in 0–5% NaCl. *B. odysseyi* grows at pH 6–10 (optimum at pH 7) and 25–42° C. (optimum 30–35° C.). With the exception of arabinose, breakdown of sugars to acids does not occur following prolonged incubation. *B. odysseyi* prefers pyruvate, amino acids, purine or pyrimidine bases and related compounds as carbon and energy sources. *B. odysseyi* is catalase-positive, but does not produce gelatinase, arginine dihydrolase, lysine or ornithine decarboxylase, lipase, amylase or alginase. The organism does not produce $H_2S$ from thiosulfite and is not involved in denitrification. The type strain, strain 34hs-1 (=ATCC PTA-4993$^T$=NRRL B-30641=NBRC 100172$^T$), was isolated from the surface of the Mars Odyssey spacecraft.

What is claimed is:

1. An isolated biologically pure culture of *Bacillus odysseyi* strain 34hs-1 deposited under accession number NRRL B-30641.

* * * * *